(12) United States Patent
Fawcett

(10) Patent No.: US 7,052,481 B2
(45) Date of Patent: May 30, 2006

(54) BALLOON CATHETER INFLATION

(75) Inventor: Steven Fawcett, Surrey (GB)

(73) Assignee: Biocompatibles LTD, Surrey (GB)

( * ) Notice: Subject to any disclaimer, the term of this patent is extended or adjusted under 35 U.S.C. 154(b) by 0 days.

(21) Appl. No.: 10/061,268

(22) Filed: Feb. 4, 2002

(65) Prior Publication Data

US 2002/0115962 A1 Aug. 22, 2002

(30) Foreign Application Priority Data

Feb. 2, 2001 (GB) ................................ 0102726.7

(51) Int. Cl.
*A61M 25/14* (2006.01)
(52) U.S. Cl. ................................ 604/100.01; 604/99.01
(58) Field of Classification Search .. 604/99.01–99.04, 604/98.01, 97.02, 100.01, 68–72
See application file for complete search history.

(56) References Cited

U.S. PATENT DOCUMENTS

| 4,654,027 A | * | 3/1987 | Dragan et al. ........... 604/99.03 |
| 5,423,770 A | * | 6/1995 | Yoon ......................... 604/506 |
| 5,993,412 A | * | 11/1999 | Deily et al. .................... 604/68 |

* cited by examiner

*Primary Examiner*—Nicholas D. Lucchesi
*Assistant Examiner*—Laura A Bouchelle
(74) *Attorney, Agent, or Firm*—Sughrue Mion, PLLC

(57) ABSTRACT

A balloon catheter comprising a fluid dispensing device. The device comprises a housing defining a chamber for retaining, in use, balloon inflation fluid. An outlet attaches, in use, to a catheter inflation lumen, and dispensing means dispenses fluid, in use, from the chamber via the outlet into the catheter lumen. An indicator indicates when a predetermined volume of fluid has been dispensed from the outlet.

10 Claims, 4 Drawing Sheets

BALLOON CATHETER INFLATION

This invention relates to balloon catheters of the type used for insertion into the lumen of a human or animal body. In particular, it relates to a balloon catheter having a device for controlling the inflation of the balloon catheter.

Balloon catheters are well known in the art. They are available in various sizes for a variety of medical applications. Generally they comprise an elongate body which has, at its distal end, a balloon which can be inflated when appropriately positioned within a body lumen by delivery of an inflating fluid. The main purpose of their use is to re-open occluded lumens, such as arteries, which may have started to close due to build-up of deposits on the walls of the lumen in question.

Whilst having become very popular for use in various types of surgery, such balloon catheters have a number of problems associated with them. One such problem is that of inflation of the balloon. Because, by their very nature, the balloons of such catheters are inflated in remote locations in a body which are difficult to monitor, it can be extremely difficult to provide accurate sensing of inflation levels within such balloons. To monitor the inflation of the balloon it is therefore common to monitor the pressure of the fluid applied to the catheter to inflate the balloon and use this as an indication of balloon inflation. Such an approach has problems, however. Firstly, it may be that the catheter has an obstruction which results in an increase in pressure even though an adequate amount of fluid has not been delivered to the balloon to ensure inflation. Secondly, inadequate inflation of the balloon may occur if a particularly rigid obstruction is being opened up and pressure will not indicate that this is the case.

The above invention seeks to overcome some of the above problems.

According to the present invention there is provided a balloon catheter comprising a balloon arranged to be inflated, in use, by fluid delivered thereto via a lumen fluid dispensing device attached to the lumen and comprising:

a housing defining a chamber for retaining, in use, balloon inflation fluid;

an outlet attached to the lumen;

dispensing means for dispensing fluid, in use, from the chamber via the outlet into the catheter lumen; and an indicator for indicating when a predetermined volume of fluid has been dispensed from the outlet.

The outlet may comprise a pressure activated seal which opens when a predetermined fluid pressure is exceeded by the fluid contents of the chamber in use.

The indicator may be a simple graduated window and internal marker configuration, or may comprise an internal sensor attached to an external display such as a liquid crystal display.

The dispensing means may be a plunger which may be attached to an external removable plunger key to prevent inadvertent dispensing of fluid. The dispensing means may be provided with a lock. The dispensing means, if a plunger is employed, may have biassing means associated therewith. A portion of the plunger of the dispensing means may act as a component of the indicator.

The catheter may comprise an inlet valve so that fluid can be inserted into the chamber to prime the device.

The present invention allows a user to inflate a balloon catheter with reference to a fixed volume accurately calibrated to the balloon and ensures that enough fluid is dispensed to ensure complete expansion of the balloon even if a particularly rigid obstruction is being expanded. The present invention also provides for a sealed dispensable unit to prevent contamination, although with the provision of an additional valve it can enable the provision of a dispenser that is able to dispense fluid with a short shelf life. Furthermore, the provision of the fluid in a discrete component that is integral with the balloon catheter reduces the need to have additional equipment available to a surgeon during operation as well as reducing the overall cost of the equipment.

Examples of the present invention will now be described with reference to the accompanying drawings, in which.

Figure 1:
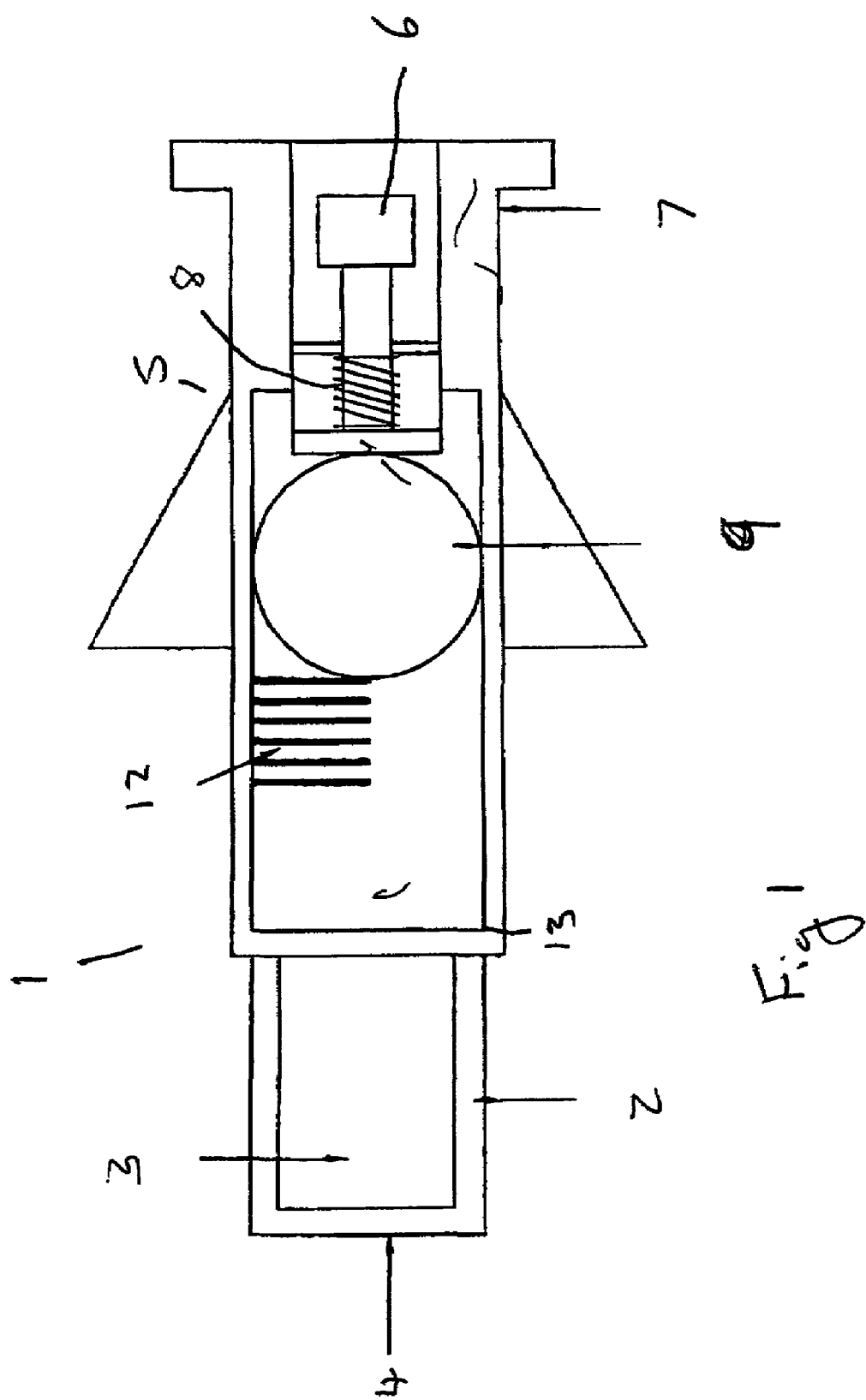
FIG. 1 is a side schematic cross-sectional view of a device forming part of a catheter according to the present invention.
Figure 2:
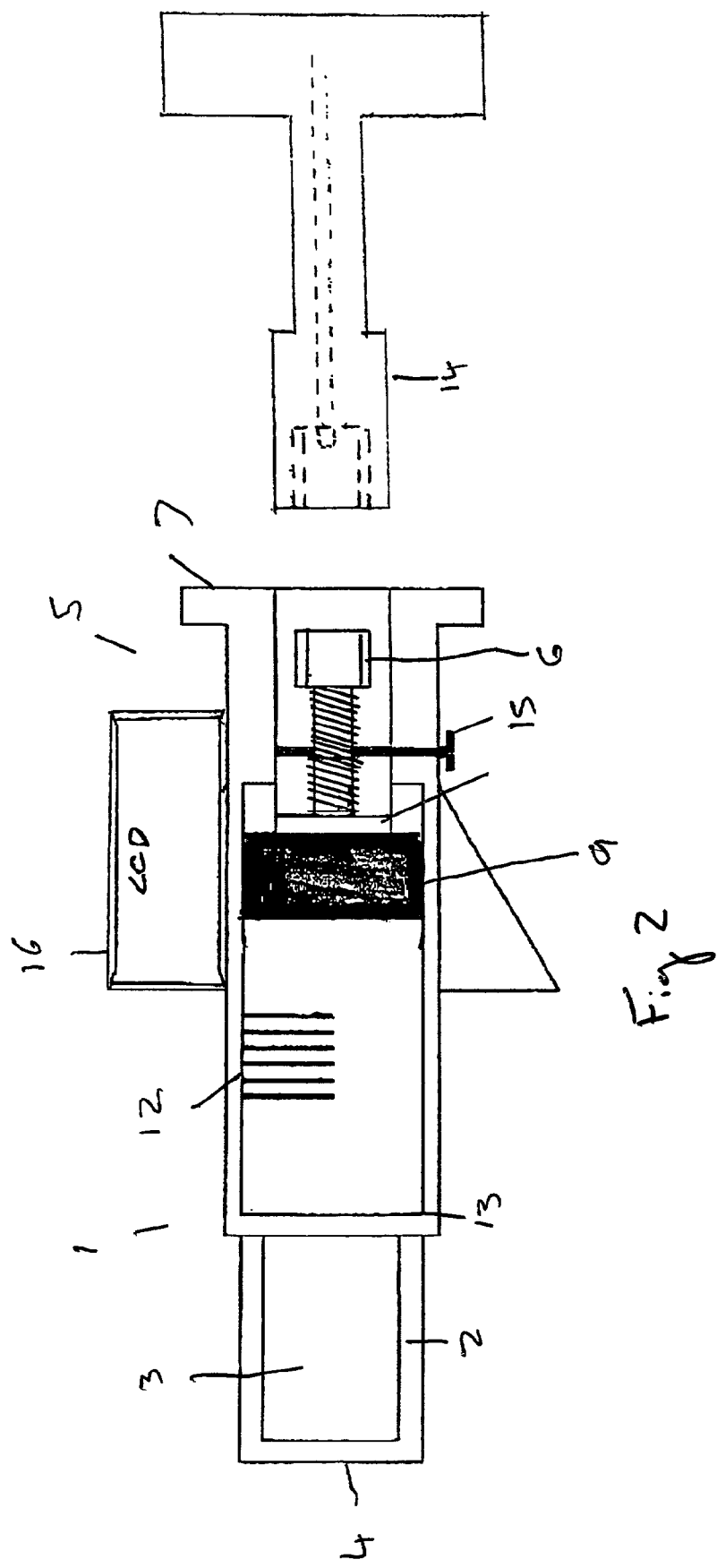
FIG. 2 is a schematic side cross-sectional view of a second example device forming part of a catheter according to the present invention.
Figure 4:
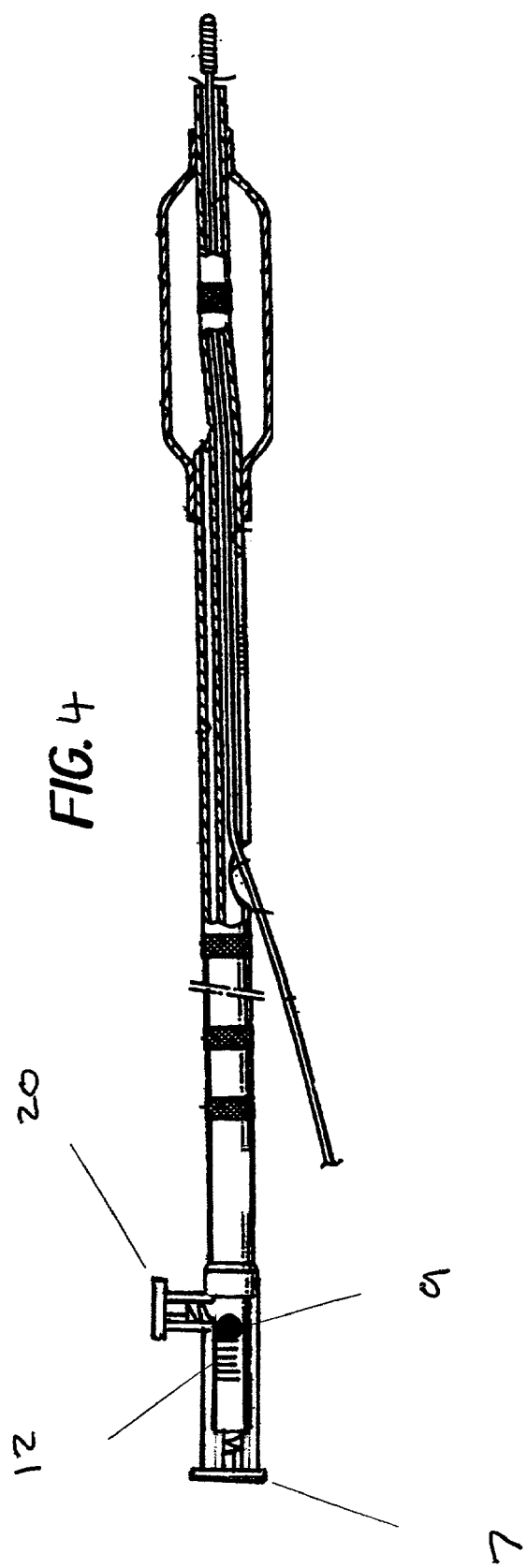
FIG. 4 is a side schematic partial cross-sectional view of a catheter according to the present invention.

FIG. 1 is a side schematic cross-sectional view of a device 1 forming part of a balloon catheter according to the present invention. The device 1 has a housing 2 which defines a fluid-containing chamber 3. An outlet 4 is attached to the lumen 11 of a catheter 10 (FIG. 4). As mentioned above, the outlet 4 may be blocked by a tamper-evident seal that is broken when sufficient pressure is applied to it via fluid in the chamber 3. A dispensing section 5 comprises a plunger 6 disposed within a valve housing 7 in such a manner that it can slide within the housing 7 upon application of external pressure to it in the direction of the outlet 4. In this example the plunger 6 is biassed by a spring 8 in the direction of the outlet 4 to reduce the necessary force that needs to be applied by an operator in use, although in many cases this spring may be unnecessary or even undesirable. The plunger 6 drives, in use, a piston, which in this example is provided by a Teflon (RTM) ball. In use, movement of the plunger 6 drives the ball 9 towards the outlet 4 and urges fluid in the chamber 3 to the lumen 11 (FIG. 4) of a catheter 10 (FIG. 4). A portion 12 of the housing is transparent and may be graded, so that an operator can view movement of the ball 9 and hence determine when appropriate volume of fluid has been dispensed by the outlet 4. A final stop 13 may be provided to prevent excess fluid being dispensed from the chamber. FIG. 2 shows a further example of the invention, in which components that correspond to those in FIG. 1 are numbered identically. In this example, the ball 9 is replaced with a piston 9 which is, again, driven by a plunger 6. An actuating key 14 must be applied to the plunger 6 before operation can be achieved. Furthermore, in this example an optional locking key 15 is provided to prevent accidental actuation of the device 1. In this example, a display that may be a liquid crystal display 16 is provided to optionally provide a volumetric output to increase the accuracy of the dispense volume reading.

Figure 3:
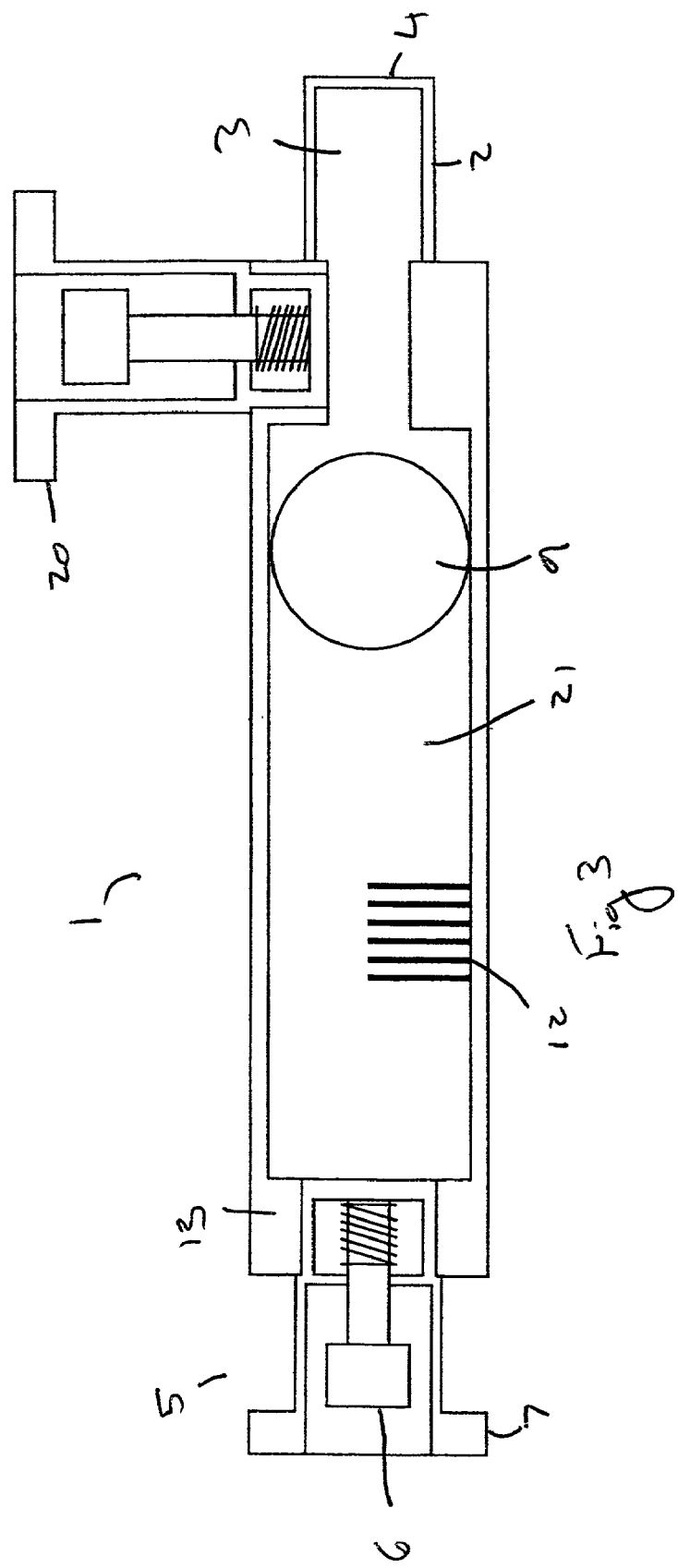
FIG. 3 is a schematic side cross-sectional view of a third example device forming part of a catheter according to the present invention.

FIG. 3 shows a further example device according to the invention in which, again, components which correspond to those in the example of FIG. 1 are numbered identically. In this example, however, a valve 20 is provided so that fluid can be inserted into the chamber 3. This provides a device 1 which can be filled on site so that fluid with a limited shelf life can be dispensed from the device. In operation, fluid is input via the valve 20 and fluid in the region 21 of the housing 2 is evacuated via the dispensing region 5 so that the ball piston 9 moves back toward the dispensing region until it engages with the plunger 6. The valve 20 is configured so that it will not allow outward flow of fluid, and the plunger can then be moved in the direction of the outlet 4 to dispense fluid from the chamber 3.

FIG. 4 shows an example catheter 10 that may be employed with the invention. The catheter has a hub 30 which is attached to the devices of FIGS. 1 to 3. In the hub 30 is a fluid inlet which connects with a fluid lumen 11, which in turn connects with the interior of a balloon 31. A lumen 32 passes through the lumen 31 so that a guide wire 32 can be inserted therein to guide the catheter 10 to a desired location in use. In operation, the catheter may be placed in position and then the device 1 of the invention attached to the hub 4, and fluid dispensed by operation of the dispensing region 5 to inflate the balloon 31. Optimum inflation in ensured because of the ability to measure a precise volume of fluid. The dispensing device is provided for a specific balloon type so, for improved safety, optimum inflation can be ensured for the device and the likelihood of operator error reduced.

The invention claimed is:

1. A balloon catheter, comprising:
   a balloon arranged to be inflated, in use, by fluid delivered thereto via a lumen, and
   a fluid dispensing device attached to the lumen, the fluid dispensing device comprising:
   a housing having a wall defining a chamber for retaining inflation fluid, the housing having a first end and a second end, the second end of the housing in fluid communication with the lumen, wherein the wall includes a transparent portion;
   an indicator movably disposed within the housing, wherein the indicator is movable between a first position and a second position to indicate a volume change of inflation fluid within the chamber; and
   a plunger in communication with the first end of the housing, wherein the plunger is movable between a first position and a second position to displace fluid from said housing into said lumen to inflate the balloon.

2. The balloon catheter according to claim 1, wherein the indicator comprises an internal sensor attached to an external display.

3. The balloon catheter according to claim 1, wherein the plunger is attached to an external removable plunger key to prevent inadvertent dispensing of fluid.

4. The balloon catheter according to claim 1, wherein the plunger includes a biasing spring.

5. The balloon catheter according to claim 1, wherein the fluid dispensing device is provided with a lock.

6. The balloon catheter according to claim 1, further comprising an inlet valve that is provided on the housing such that fluid can be inserted into the chamber, in use, to prime the device.

7. The balloon catheter according to claim 1, wherein movement of the indicator is visible through the transparent portion of the housing.

8. The balloon catheter according to claim 1, further including a pressure activated seal disposed within the second end of the housing and in fluid communication with the lumen.

9. The balloon catheter according to claim 8, wherein the pressure activated seal is configured to open when a predetermined fluid pressure is achieved within the chamber through movement of the plunger.

10. The balloon catheter according to claim 1, wherein the transparent portion of the housing includes graduated markings disposed thereon.

* * * * *